(12) United States Patent
McIlroy et al.

(10) Patent No.: US 7,992,570 B2
(45) Date of Patent: Aug. 9, 2011

(54) FRACTIONATED LIGHT PDT THERAPY FOR POSTERIOR EYE DISEASE

(75) Inventors: Brian William McIlroy, Sammanish, WA (US); Gregory Heacock, Auburn, WA (US); Paula A. Mahoney, Woodinville, WA (US); Andrew Michael Peter Hamilton, Pinner (GB)

(73) Assignee: Light Sciences Oncology, Inc., Snoqualmie, WA (US)

( * ) Notice: Subject to any disclaimer, the term of this patent is extended or adjusted under 35 U.S.C. 154(b) by 1872 days.

(21) Appl. No.: 11/089,944

(22) Filed: Mar. 25, 2005

(65) Prior Publication Data
US 2005/0240247 A1 Oct. 27, 2005

Related U.S. Application Data

(60) Provisional application No. 60/564,808, filed on Apr. 22, 2004.

(51) Int. Cl.
*A61B 19/00* (2006.01)

(52) U.S. Cl. .......................................... 128/898; 607/88

(58) Field of Classification Search .................. 606/4–6; 607/88, 89, 92; 128/898
See application file for complete search history.

(56) References Cited

U.S. PATENT DOCUMENTS

| | | | |
|---|---|---|---|
| 6,319,273 B1 | 11/2001 | Chen et al. | |
| 6,524,330 B1 | 2/2003 | Khoobehi et al. | |
| 6,830,567 B2 * | 12/2004 | Schuele et al. | 606/4 |
| 6,840,933 B1 | 1/2005 | Pang et al. | |
| 6,936,043 B2 * | 8/2005 | Peyman | 606/4 |
| 6,942,655 B2 * | 9/2005 | Peyman | 606/4 |
| 2002/0094998 A1 * | 7/2002 | Burke et al. | 514/396 |
| 2003/0167033 A1 * | 9/2003 | Chen et al. | 604/20 |

\* cited by examiner

*Primary Examiner* — Ahmed M Farah
(74) *Attorney, Agent, or Firm* — McAndrews, Held & Malloy, Ltd.

(57) ABSTRACT

A method and system directs therapeutic light of a first wavelength to a patient's eye to excite a photosensitizing agent for PDT during a series of discrete periods of time that are separated by non-therapeutic intervals. Diagnostic light of a second wavelength can be directed to the eye during at least a portion of one or more of the non-therapeutic intervals to allow a physician to see the affect of the therapy.

15 Claims, 3 Drawing Sheets

FRACTIONATED LIGHT PDT THERAPY FOR POSTERIOR EYE DISEASE

CROSS-REFERENCE TO RELATED APPLICATIONS

The present application claims the priority of Provisional Patent Application Ser. No. 60/564,808 filed Apr. 22, 2004. That application is hereby incorporated herein by reference.

STATEMENT REGARDING FEDERALLY SPONSORED RESEARCH OR DEVELOPMENT

N/A

TECHNICAL FIELD

The present invention relates, in general, to treatment of ocular disease, and, in particular, to a system and method for excitation of photoreactive or photosensitive agents in eye tissue.

BACKGROUND OF THE INVENTION

Many eye diseases are currently treated with lasers or other similar visible light sources. The most common treatments involve thermal destruction of areas of diseased cells within the eye. When the diseased cells are destroyed local progression of the disease is stopped and in some cases, cellular signaling induces a healing response and healthy cells replace the diseased ones. A drawback to these common thermal therapeutic techniques is due to the proximity of the diseased cells to the healthy cells. During the course of the therapeutic treatment, many healthy cells are unintentionally destroyed due to the imprecise thermal effect of the laser.

In an attempt to reduce unintentional thermal damage to proximal cells, a new therapeutic technique is currently gaining prominence. The new technique is called Photodynamic Therapy (PDT). Photodynamic therapy or PDT is a process whereby light of a specific wavelength or waveband is directed to tissues undergoing treatment or investigation that have been rendered photosensitive through the administration of a photoreactive or photosensitizing agent. In this therapy, a photoreactive agent having a characteristic light absorption waveband is first administered to the patient, typically either orally or by injection or even by local delivery to the treatment site. Proliferating cells, such as those involved in many eye diseases, may preferentially take up or absorb a number of or many photosensitizing agents. Once the drug or photosensitizing agent has been administered and reaches the targeted tissue, the tissue is illuminated with light of an appropriate wavelength or waveband corresponding to the absorption wavelength or waveband of the photoreactive agent.

The objective of the PDT may be either diagnostic, where the energy level and wavelength of light is selected to cause the photoreactive agent to fluoresce, thus yielding information about the tissue without damaging the tissue, or therapeutic, where the wavelength of light delivered to the photosensitive tissue under treatment causes the photoreactive agent to undergo a photochemical interaction with oxygen in the tissue under treatment yielding free radical species such as singlet oxygen, causing local tissue effect.

In PDT therapies, the photosensitizing agent or drug is injected into the body of the patient, and then light at lower than thermal energy levels is focused onto the diseased cells. In these therapies, targeted cells are affected by oxidative damage that is initiated by illumination of the photosensitizing agent. However, a problem exists in that the drug photosensitizing agent may distribute to all tissues and if the application of light is not controlled, areas where the therapy is not desired may be negatively affected.

BRIEF SUMMARY OF THE INVENTION

In accordance with the present invention, the disadvantages of prior systems and methods for treating diseased cells of the eye have been overcome. In accordance with the present invention, therapeutic light of a first wavelength is directed to a patient's eye to excite a photosensitizing agent during a series of discrete periods of time that are separated by non-therapeutic intervals.

In accordance with one embodiment of the system and method of the present invention, light of a first wavelength or waveband for exciting a photosensitizing agent in targeted eye tissue is directed to the patient's eye for a first predetermined period of time. The system and method of this embodiment of the invention then stops directing the light of the first wavelength or waveband for a second predetermined period of time to allow the targeted tissue to re-oxygenate. After the second period of time, the method and system of this embodiment resume directing light of the first wavelength or waveband to the patient's eye to continue to excite the photosensitizing agent.

In accordance with another embodiment of the method and system of the present invention, therapeutic light of a first energy level is directed to a patient's eye for a first period of time to excite the administered photosensitizing agent to undergo a photochemical interaction with oxygen. During a second period of time, following the first period of time, the energy level of the therapeutic light directed to the eye is reduced to a level that allows the eye tissues to re-oxygenate. After the second period of time, therapeutic light of the first energy level is again directed to the eye to continue the therapy. It is noted, that in this embodiment, the energy level of the therapeutic light during the second period of time may be reduced to zero or to an energy level that is below the therapeutic level that causes the PDT effect.

In accordance with a further embodiment of the present invention, therapeutic light of a first wavelength or waveband for exciting a first photosensitizing agent is directed to a patient's eye for a first period of time. Thereafter, diagnostic light of a second wavelength or waveband is directed to a patient's eye for a second period of time. After the second period of time, the therapeutic light is again directed to the patient's eye. During the second period of time a physician may see the affect of the therapy.

These and other advantages and novel features of the present invention, as well as details of an illustrated embodiment thereof, will be more fully understood from the following description and drawings.

DETAILED DESCRIPTION OF THE INVENTION

Figure 1:
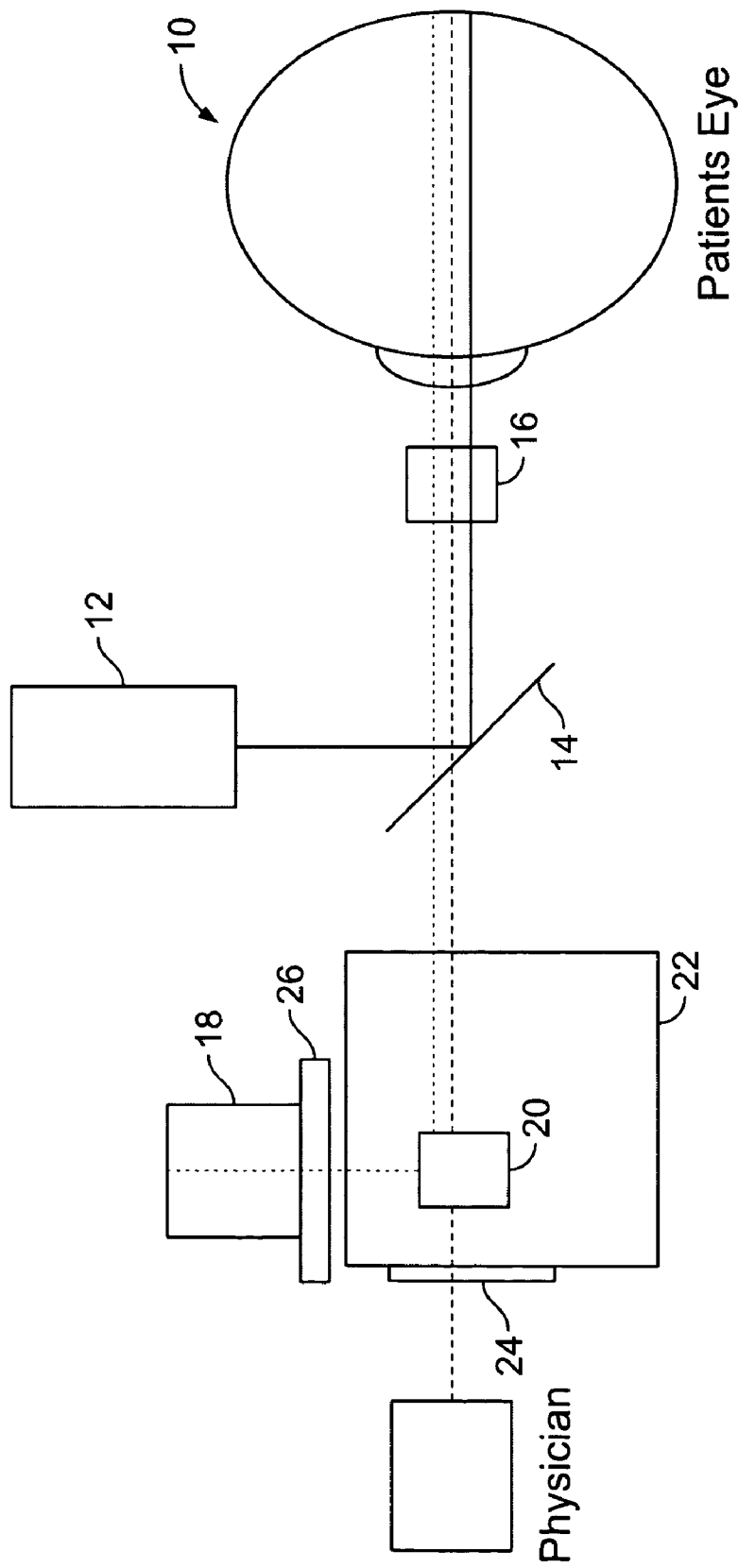
FIG. 1 is an illustration of the optical system of one embodiment of the present invention for directing therapeutic and diagnostic light to a patient's eye.

A system for directing therapeutic and diagnostic light for Photodynamic Therapy (PDT) to a patient's eye 10 in accordance with one embodiment of the present invention is shown in FIG. 1. Therapeutic light from a therapeutic light source 12 is reflected by a dichroic mirror 14 to a therapeutic contact lens 16, such as a Mainster lens (Ocular Instruments, USA) which in turn directs the therapeutic light to the patient's eye 10. The therapeutic light source 12 may be, for example, a light emitting diode (LED) that emits light in a waveband centered about a wavelength of 664 nm. The dichroic mirror 14 is such that the mirror reflects light in the waveband of the therapeutic light source and passes therethrough light of substantially all other wavelengths.

When the therapeutic light from the source 12 is delivered to eye tissue that has been made photosensitive by the administration of a photoreactive or photosensitizing agent to the patient, the photosensitive agent undergoes a photochemical interaction with oxygen such that the targeted cells are affected by oxidative damage. In accordance with the present invention, the therapeutic light source 12 is controlled to direct the therapeutic light to the mirror 14 and thus to the eye 10 during a series of discrete periods of time that are separated by non-therapeutic intervals. In one embodiment, during the non-therapeutic intervals, no therapeutic light is directed to the eye 10. Alternatively, the level of therapeutic light 12 that is generated may be reduced during the non-therapeutic intervals to a level that is sufficiently low such that no PDT affects occur. Preferably, the reduced energy level during the non-therapeutic intervals is zero or sufficiently low to allow the targeted tissue to re-oxygenate.

The system 10 also includes a slit lamp illuminator 18 that provides a source of white light. The light from the illuminator 18 is reflected by a small reflecting cube 20 to the dichroic mirror 14. The illumination light passes through the dichroic mirror 14 and through the therapeutic contact lens 16 to illuminate the patient's eye 10. Light reflected from the patient's eye passes back through the contact lens 16 and the dichroic mirror 14 to the slit lamp optical system 22. The reflected illumination light then passes around the small cube 20 to a pair of lenses 24 into which a physician or observer looks to observe the patient's eye.

In a preferred embodiment, a first photosensitizing agent is administered to the patient wherein this photosensitizing agent is excited by the wavelength of therapeutic light from the source 12 in the discrete therapeutic periods of time that are separated by non-therapeutic intervals. After a discrete therapeutic period of time, and during the non-therapeutic interval, a fluorescent agent or dye may be administered to the patient's eye 10. Thereafter, and during the non-therapeutic interval, a filter 26 is disposed in the optical path between the slit lamp illuminator 18 and the dichroic mirror 14. The filter 26 is such that it passes diagnostic light of a wavelength that will excite the fluorescent agent. For example, the light passed by the filter 26 may have a wavelength of approximately 485 nm. When this diagnostic light excites the fluorescent agent, the light emitted by the excited fluorescent has a wavelength of approximately 530 nm. The emitted light is passed through an analyzer filter that passes light with a wavelength of approximately 530 nm to the lenses 24 into which the physician or observer looks. As such the physician or observer can see the affect of the treatment by the therapeutic light source 12 during the non-therapeutic interval.

After the non-therapeutic interval, the light source 12 is again controlled to generate therapeutic light that is directed to the patient's eye for PDT. In accordance with the present invention, there may be two or more discrete therapeutic periods where the discrete therapeutic periods are separated by non-therapeutic intervals.

In one embodiment, the filter 26 is disposed between the slit lamp illuminator 18 and the small reflecting cube 20 and the analyzer filter is disposed between the cube 20 and the dichroic mirror 14. In an alternative embodiment, the filter 26 and analyzer filter are combined such that the three filters are aligned in a row with the center filter being the 485 nm filter 26 and the two outside filters being the 530 nm analyzer filters. In this embodiment, light having a wavelength of 485 nm is passed by the center filter to the eye 10 during the non-therapeutic interval and light having a wavelength of 530 nm emitted from the excited fluorescent in the eye 10 is passed by the two 530 nm filters to the lenses 24 for observation by the physician during the non-therapeutic interval.

Figure 2A:
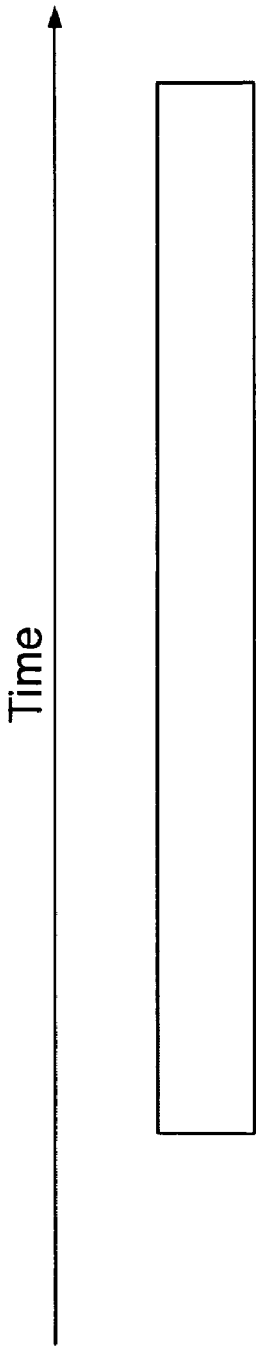
FIGS. 2A-B are timing diagrams respectively illustrating a continuous application of therapeutic light and the application of therapeutic light for PDT in a series of discrete time periods separated by non-therapeutic light intervals.
Figure 2B:
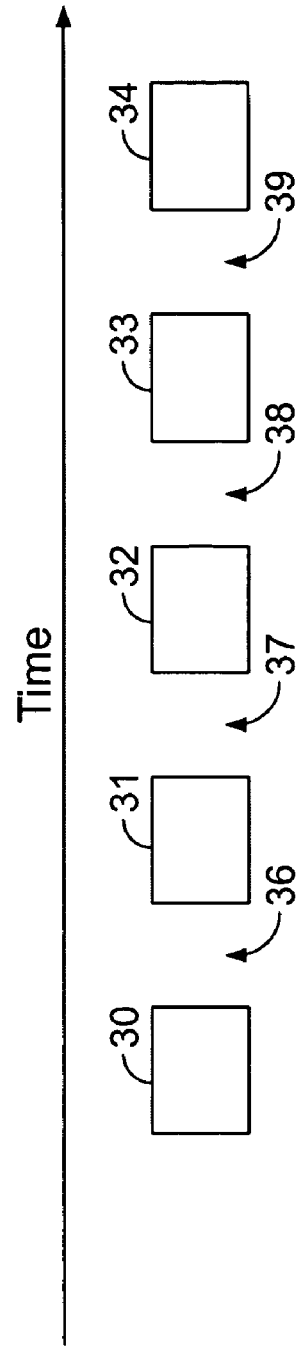

FIG. 2A illustrates a conventional PDT therapy in which the therapeutic light is continuously directed to the eye. The total energy delivered in the continuous therapy depicted in FIG. 2A may be, for example, 100 J/cm$^2$. FIG. 2B illustrates the method of providing therapy during discrete periods of time in accordance with the present invention. In particular, in this embodiment depicted in FIG. 2B, there are five discrete sequential periods 30-34 during which therapeutic light is directed to the eye 10. Each of the discrete therapeutic periods 30-34 may deliver energy of 12 J/cm$^2$ to provide a total energy delivered of 60 J/cm$^2$. During the non-therapeutic intervals 36-39 separating the sequence of therapeutic periods 30-34, no therapeutic light is directed to the eye 10. Alternatively, as discussed above, therapeutic light of a substantially reduced energy level, such that no PDT affect is caused, is generated during the non-therapeutic intervals. As can be seen, one benefit of the embodiment of the present invention as depicted in FIG. 2B is that the total energy delivered to all cells of the eye is less than the amount of energy delivered in the continuous manner shown in FIG. 2A although the PDT therapeutic effects of the two methods are equivalent. Therefore healthy cells are not overexposed to light and yet targeted cells received the desired treatment. An additional benefit is that the non-therapeutic intervals 36-39 may be utilized so that the effect of the applied therapy can be easily seen with diagnostic light.

Figure 3A:
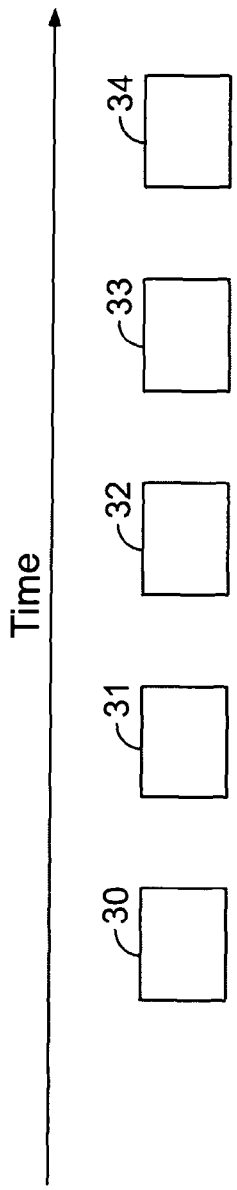
FIGS. 3A-B are timing diagrams respectively illustrating a series of discrete therapeutic light periods and a series of discrete therapeutic light periods with diagnostic light periods in the non-therapeutic light intervals.
Figure 3B:
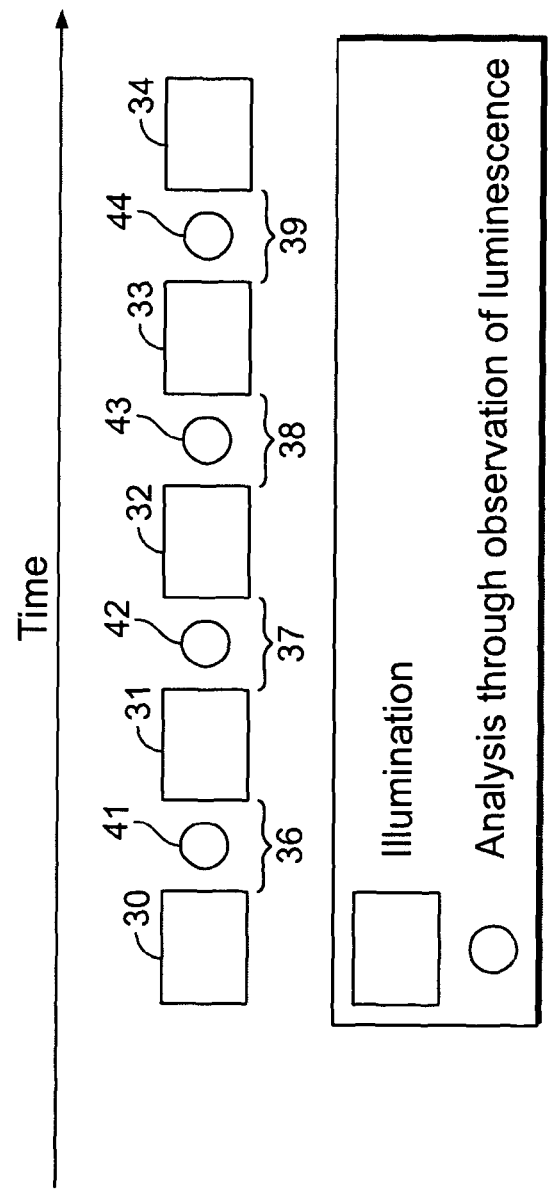

FIG. 3A illustrates the series of discrete therapy periods 30-34 as depicted in FIG. 2B. FIG. 3B illustrates an alternative embodiment in which the diagnostic light of, for example, 485 nm is directed to the patient's eye 10 during periods 41-44 in the respective non-therapeutic intervals 36-39 after a fluorescent agent is administered to the eye 10 so that a physician or observer can see the affects of the treatment in the intervening non-therapeutic intervals.

As an example, a PDT photosensitizing agent of mono-1-aspartyl chlorine e6 may be administered by IV or locally. The light source 12 then delivers energy at 664 nm for a therapeutic period, i.e., a discrete period that is sufficient to excite the PDT photosensitizing agent, which may be for example 40 seconds. Thereafter, fluorescein may be administered to the eye and the 485 nm filter positioned between the light source 18 and mirror 14 to direct light of that wavelength to the eye. At the same time the analyzer filters are positioned to pass light with a 530 nm wavelength emitted form the excited fluorescein to the lenses 24 so that an observer can see the effect of the therapy in the non-therapeutic interval. The non-therapeutic interval may be, for example, in the range of 10-40 seconds to allow the eye tissue to re-oxygenate in between the discrete therapy periods.

Many modifications and variations of the present invention are possible in light of the above teachings. Thus, it is to be understood that, within the scope of the appended claims, the invention may be practiced otherwise than as described hereinabove.

The invention claimed is:

1. A method for treating and/or diagnosing a disease of a patient's eye comprising:
   administering a first photosensitizing agent to a patient;
   directing to the patient's eye for a first predetermined period of time therapeutic light of a first wavelength or waveband for exciting the first photosensitizing agent;
   administering a second agent to a patient;
   directing to the patient's eye for a second predetermined period of time diagnostic light of a second wavelength or waveband for exciting the second agent, the diagnostic light being directed to the eye at a time after the end of the first period of time; and
   resuming the direction of the therapeutic light to the patient's eye at a time after the end of the second period of time.

2. A method for treating and/or diagnosing a disease of a patient's eye as recited in claim 1 wherein the second agent includes a fluorescent dye.

3. A method for treating and/or diagnosing a disease of a patient's eye as recited in claim 2 including passing light of a third wavelength emitted by an excited fluorophore so that the light of the third wavelength can be seen by an observer and filtering other wavelengths of light so that they are not observed.

4. A method for treating and/or diagnosing a disease of a patient's eye as recited in claim 1 wherein the resuming the direction of the therapeutic light to the patient's eye occurs in a range of about 10-40 seconds after the end of the first predetermined period of time.

5. A method for treating and/or diagnosing a disease of a patient's eye as recited in claim 1 including passing, through a filter to an observer, light of a third wavelength or waveband emitted by fluorescence by the second agent so that the light of the third wavelength or waveband can be seen by the observer and filtering other wavelengths of light so that they are not observed.

6. A method for treating and/or diagnosing a disease of a patient's eye as recited in claim 5 wherein the wavelength of the light emitted by the second agent and passed for observation is about 530 nm.

7. A method for treating and/or diagnosing a disease of a patient's eye as recited in claim 1 wherein the therapeutic light has a waveband centered approximately about 664 nm.

8. A method for treating and/or diagnosing a disease of a patient's eye as recited in claim 1 wherein the diagnostic light has a wavelength of about 485 nm.

9. A method for treating and/or diagnosing a disease of a patient's eye comprising:
   administering a photosensitizing agent to a patient, the photosensitizing agent being absorbed in targeted eye tissue; and
   directing therapeutic light to a patient's eye to excite the photosensitizing agent in the targeted tissue during a series of discrete periods of time during a single treatment that are separated by at least one non-therapeutic interval, wherein the at least one non-therapeutic interval comprises a first non-therapeutic interval having a duration of about 10 seconds or longer to allow eye tissue to re-oxygenate.

10. A method for treating and/or diagnosing a disease of a patient's eye as recited in claim 9 including administering a fluorescent agent to the eye; and directing, during at least a portion of one of the at least one non-therapeutic interval, diagnostic light to the patient's eye to excite the fluorescent agent.

11. A method for treating and/or diagnosing a disease of a patient's eye as recited in claim 10 including passing light of a third wavelength emitted by the excited fluorescent agent so that the light of the third wavelength can be seen by an observer and filtering other wavelengths of light so that they are not observed.

12. A method for treating and/or diagnosing a disease of a patient's eye as recited in claim 11 wherein the wavelength of the light emitted by the fluorescent agent and passed for observation is about 530 nm.

13. A method for treating and/or diagnosing a disease of a patient's eye as recited in claim 10 wherein the therapeutic light has a waveband centered approximately about 664 nm.

14. A method for treating and/or diagnosing a disease of a patient's eye as recited in claim 10 wherein the diagnostic light has a wavelength of about 485 nm.

15. A method for treating and/or diagnosing a disease of a patient's eye as recited in claim 9 wherein the first non-therapeutic interval has a duration of about 10-40 seconds.

* * * * *